Figure 1:
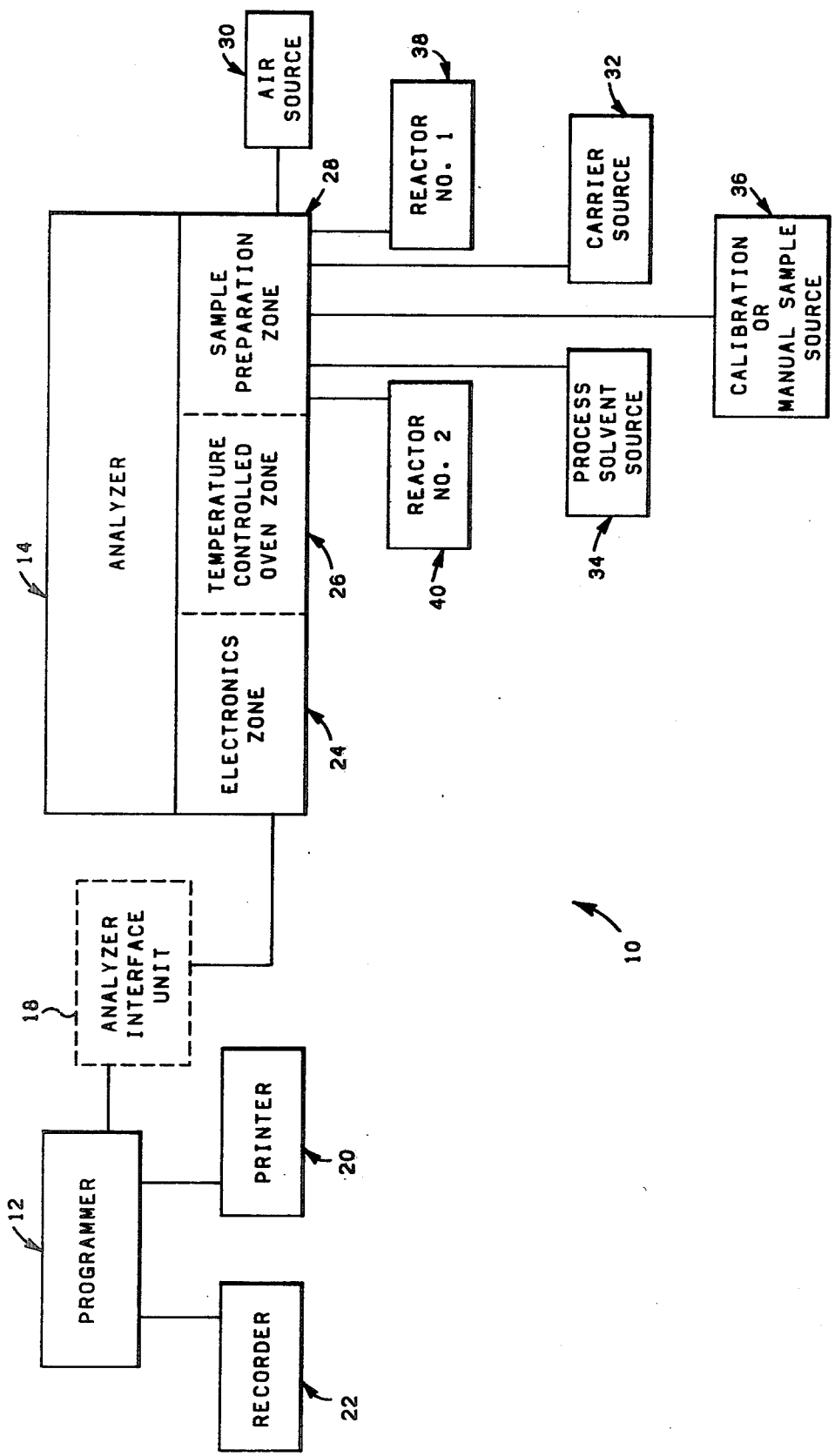

United States Patent [19]

Porter et al.

[11] 4,186,607

[45] Feb. 5, 1980

[54] LIQUID SAMPLE DILUTION SYSTEM

[75] Inventors: Grady T. Porter; Edward N. Fuller; Lewis B. Roof, all of Bartlesville, Okla.

[73] Assignee: Phillips Petroleum Company, Bartlesville, Okla.

[21] Appl. No.: 949,288

[22] Filed: Oct. 6, 1978

[51] Int. Cl.² .................................................. G01N 1/10
[52] U.S. Cl. .................................................. 73/422 GC
[58] Field of Search .......................... 73/422 GC, 1 G

[56] References Cited

U.S. PATENT DOCUMENTS

| | | | |
|---|---|---|---|
| 3,911,723 | 10/1975 | Ritter | 73/1 G |
| 4,070,913 | 1/1978 | Roof | 73/422 GC |
| 4,095,472 | 6/1978 | Mowery | 73/422 GC |
| 4,114,419 | 9/1978 | Kimbell | 73/1 G |

OTHER PUBLICATIONS

Ritter et al., Exponential Dilution as a Calibration Technique, Analytical Chemistry, vol. 48, No. 3, Mar. 1976, pp. 612, 619.

*Primary Examiner*—S. Clement Swisher

[57] ABSTRACT

Method and apparatus are disclosed which provide for the automatic intermittent injection of a small sample of liquid from a process liquid stream, dilution of the small quantity sample of liquid in a diluent stream, injection of a small quantity of the thus diluted liquid sample in a carrier fluid stream and analysis of the diluted liquid sample in the carrier fluid stream to determine the composition of the process liquid. Means are also disclosed for the analysis of manually prepared samples or calibration samples.

17 Claims, 2 Drawing Figures

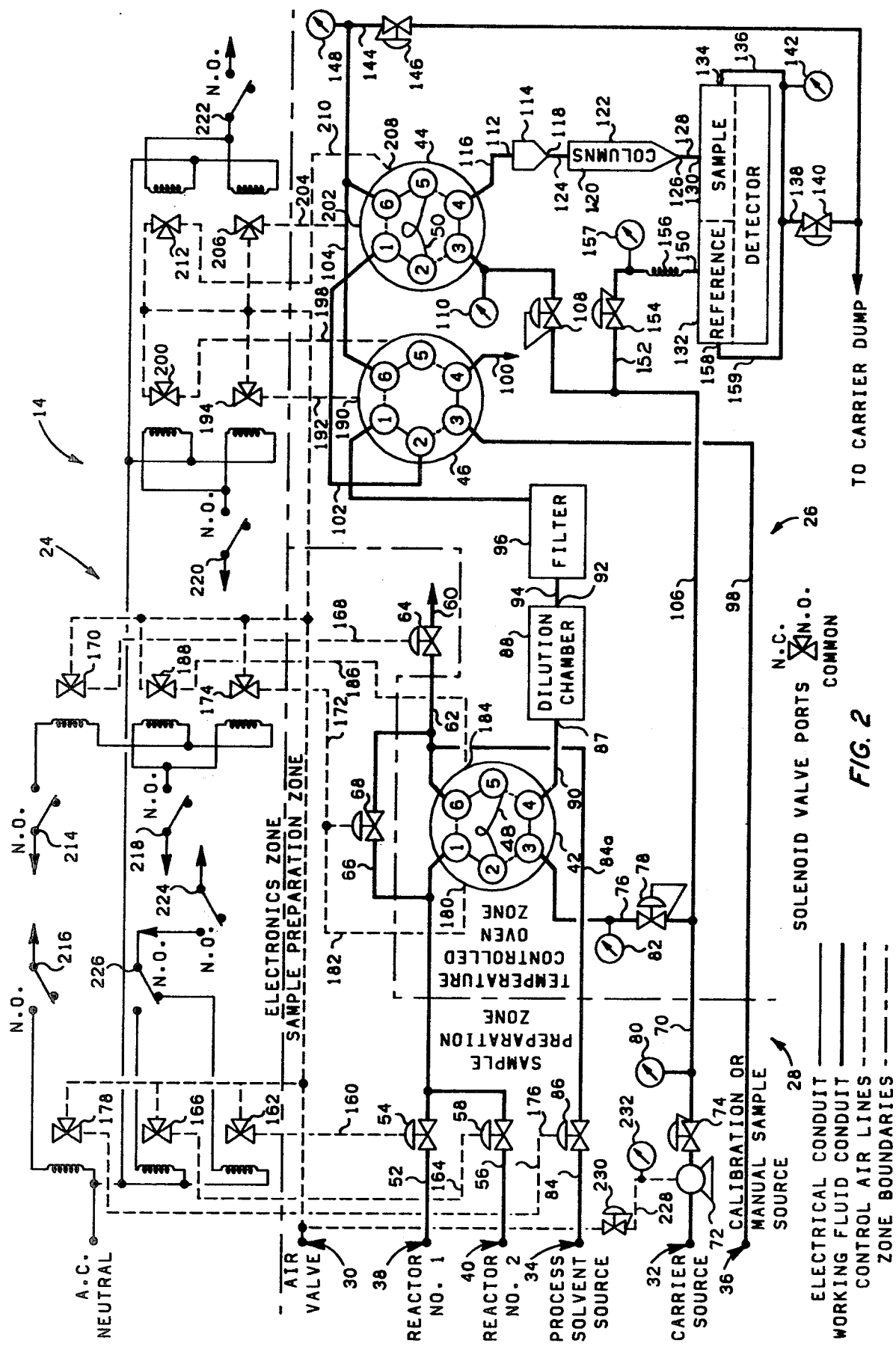

LIQUID SAMPLE DILUTION SYSTEM

This invention relates generally to the analysis of fluid samples. In one aspect the invention relates to apparatus for the preparation of a liquid sample for analysis thereof. In another aspect the invention relates to method for the preparation of a liquid sample for analysis. In still another aspect the invention relates to method and apparatus for the preparation of liquid samples for chromatographic analysis.

In the automatic sampling and analysis of fluid such as process fluids of a manufacturing plant, refinery, commercial chemical production system, or other similar process, it is often necessary to dilute the sample of process fluid prior to subjecting the sample to analysis or otherwise using the sample for a particular desired purpose. This is particularly true when the sample is so concentrated that a control dilution is necessary in order to bring the sample concentration to a level which is compatible with the use to which it will be put, or when the sample is too viscous to flow through a chromatographic column, even at high pressures. Other similar problems with high viscosity of the process fluid sampled and other similar physical and/or chemical characteristics of the sample fluid make dilution, particularly a controlled dilution in which the dilution ratio remains constant and reproducible over a long period of time during which successive samples are diluted, desirable in conjunction with many processes or production systems.

In many types of sampling apparatus, the smallest possible sample which can be taken is limited by physical constraints such as, for example, the minimum length of conduit used to connect the inlet and outlet ports of a sample loop in a sample valve. With increasing sensitivity and accuracy of modern equipment, such as chromatographic equipment, for example, it is often desirable to have even smaller samples of material to be analyzed since analysis of such smaller samples is well within the capability of the analyzing equipment, and use of smaller samples of material to be analyzed helps to shorten the time required for each analysis. By shortening the time required for each analysis cycle, an increased number of analysis cycles can be performed in a given time period thereby increasing the amount of work which can be done with a specified number of analyzers and/or increasing the resolution of process changes which may be reflectted in the analysis of process fluids.

Accordingly, it is an object of the invention to provide method and apparatus for preparation of a fluid sample. Another object of the invention is to provide method and apparatus for dilution of a fluid sample. Yet another object of the invention is to provide method and apparatus for dilution of a fluid sample for chromatographic analysis. Still another object of the invention is to provide method and apparatus for dilution of a liquid sample for liquid chromatographic analysis. Yet another object of the invention is to provide a fluid sample dilution system which allows complete purging of the sample lines between the taking of fluid samples. Still another object of the invention is to provide method and apparatus for automatically preparing process liquid samples for chromatographic analysis. Another object of the invention is to provide method and apparatus for the chromatographic analysis of fluid samples.

Other aspects, objects and advantages of the present invention will become apparent from a study of the disclosure, the appended claims and the drawing in which FIG. 1 is a schematic block diagram illustrating a chromatographic analyzer system in accordance with the present invention;

and FIG. 2 is a schematic diagram illustrating an analyzer unit in accordance with the present invention.

The dilution apparatus of the present invention comprises a first conduit with the first end thereof in fluid communication with a fluid sample source for providing a path for flow of fluid sample therethrough; a second conduit with the first end thereof in fluid communication with a diluent source for providing a path for flow of a diluent fluid stream therethrough; a first sample valve body having first, second and third inlet ports and first, second and third outlet ports, with the first inlet port thereof communicating with the second end of the first conduit and with the second inlet port thereof in fluid communication with the second end of the second conduit; a third conduit with the first end thereof in fluid communication with the first outlet port of the first sample valve body for providing a path for flow of fluid therethrough; a fourth conduit with the first end thereof in fluid communication with the second outlet port of the first sample valve body for providing a path for flow of fluid therethrough; a fifth conduit with the first end thereof in fluid communication with the third outlet port of the first sample valve body and with the second end thereof in fluid communication with the third inlet port of said first sample valve body for providing a path for flow of fluid therethrough; a first sample valve member operatively related to the first sample valve body for placing in fluid communication the first inlet port with the third outlet port, the second inlet port with the second outlet port and the third inlet port with the first outlet port, and, alternately, for placing in fluid communication the first inlet port with the first outlet port, the second inlet port with the third outlet port, and the third inlet port with the second outlet port, so as to inject a predetermined quantity of the sample fluid into the diluent liquid stream emanating from the second outlet port of the first sample valve body; dilution chamber means having inlet and outlet ports with the inlet port thereof communicating with the second end of the fourth conduit for mixing the predetermined quantity of the sample fluid with a diluent fluid stream; a sixth conduit with the first end thereof in fluid communication with the outlet port of the dilution chamber for providing a path for flow of fluid from the dilution chamber; a second sample valve body having first, second and third inlet ports and first, second and third outlet ports, with the first inlet port thereof in fluid communication with the second end of the sixth conduit; a seventh conduit with the first end thereof in fluid communication with a carrier fluid source and with the second end thereof in fluid communication with the second inlet port of the second sample valve body for providing a flow path for flow of carrier fluid from the carrier fluid source; an eighth conduit with the first end thereof in fluid communication with the first outlet port of the second sample valve body for providing a flow path for liquid from the second sample valve body; a ninth conduit with the first end thereof in fluid communication with the second outlet port of the second sample valve body for providing a flow path for fluid from the second sample valve body; a tenth conduit with the first end thereof in fluid communication with the third outlet port of the second sample valve body and with the second end thereof in fluid communication with the third inlet port of the second sample valve body for providing a path for flow of fluid therethrough; and a second sample valve member operatively related to the second sample valve body for placing in fluid communication the first inlet port of the second sample valve body with the third outlet port of the second sample valve body, the second inlet port of the second sample valve body with the second outlet port of the second sample valve body and the third inlet port of the second sample valve body with the first outlet port of the second sample valve body, and, alternately, for placing in fluid communication the first inlet port of the second sample valve body with the first outlet port of the second sample valve body, the second inlet port of the second sample valve body with the third outlet port of the second sample valve body, so as to inject a predetermined quantity of the mixed sample fluid and diluent fluid stream emanating from the dilution chamber into the carrier fluid emanating from the carrier fluid source.

Referring now to the drawing and to FIG. 1 in particular, there is disclosed therein a liquid chromatographic analyzer system generally designated by the reference character 10. The system 10 includes a programmer unit 12 and an analyzer unit 14 suitably connected by electrical conduit 16. The programmer unit 12 can be any suitable computer, but is preferably an Optichrom ® 2100 programmer available from Applied Automation, Inc., Bartlesville, Okla. Similarly, the analyzer unit 14 is preferably an Optichrom liquid chromatographic analyzer also available from Applied Automation, Inc. In the event that a programmer unit 12 other than the Optichrom 2100 programmer is employed with the analyzer unit 14, it may be necessary to employ an analyzer interface unit 18 therebetween interposed in the conduits 16. A suitable analyzer interface unit can be obtained from Applied Automation, Inc. The use of the analyzer interface unit 18 is, however, optional. The programmer unit 12 is connected to a printer 20 and to a recorder 22. While any suitable printer can be employed, it is presently preferred to utilize a digital printer with which the results of the analysis can be printed on a tape. The recorder 22 is preferably a conventional strip chart recorder.

The analyzer unit 14 comprises an electronics zone 24, a temperature controlled oven zone 26 and a sample preparation zone 28. The analyzer unit 14 is connected to a source of pressurized air 30, or it can be provided with a self-contained pressurized air source. The analyzer unit is further connected to a carrier fluid source 32, a process solvent source 34, and is provided with facility for connection to a calibration or manual sample source 36 when desired. The analyzer unit 14 is also illustrated connected to two different process reactors 38 and 40. The process reactors 38 and 40 are each capable of providing a process liquid sample stream under pressure for liquid chromatographic analysis.

Referring now to FIG. 2, there is schematically illustrated a portion of the analyzer unit 14. The analyzer unit 14 comprises a first six-port sample valve 42, a second six-port sample valve 44 and a six-port calibration or manual sample control valve 46. A detailed discussion of the construction and operation of suitable valves for use as the valves 42, 44 and 46 can be found in U.S. Pat. Nos. 3,140,615 and 3,492,873, the disclosures of which are incorporated herein by reference. Each of these valves is an air-actuated, six-port, two-position valve which can be obtained from Applied Automation, Inc., Bartlesville, Okla. In the drawing within the circle symbolizing each sample valve body, the straight solid lines indicate the flow paths within each valve when the valve member thereof is in its first position and the straight dash lines indicate the flow paths in each valve when the valve member thereof is in its second position. While the valve construction described above is presently preferred, it should be noted that any suitable valve which can handle the multiple inputs and outputs of the present system can be employed. One such valve is described in U.S. Pat. No. 2,846,121, the disclosure of which is incorporated herein by reference.

Each of the valves 42, 44 and 46 is illustrated with the ports in the valve body thereof numbered from 1 through 6. In each valve port 1 is the first inlet port, port 2 is the third outlet port, port 3 is the second inlet port, port 4 is the second outlet port, port 5 is the third inlet port, and port 6 is the first outlet port. Sample valve 42 is provided with a sample conduit or loop 48 which provides fluid flow communication outside the valve body between the third inlet port and the third outlet port of the valve body 42. Sample valve 44 is provided with a sample conduit or loop 50 which provides fluid flow communication outside the valve body between the third inlet port and the third outlet port of the valve body of sample valve 44.

The first process reactor 38 is connected via conduit 52 and an air-actuated control valve 54 to the first inlet port of the sample valve 42 to provide a path of fluid flow from the reactor 38 through the sample valve 42. Similarly, the second process reactor 40 is connected via conduit 56, air-actuated control valve 58 and conduit 52 to the first inlet port of the sample valve 42 to provide a fluid flow path for a sample liquid from the reactor 40 to the sample valve 42. The first outlet port of the sample valve 42 communicates with a suitable sample return conduit 60 via conduit 62 and an air-actuated control valve 64 to provide a flow path for sample liquid emanating from the first outlet port of the sample valve 42 to the sample return conduit 60.

The first inlet port and first outlet port of the sample valve 42 are placed in fluid flow communication via conduit 52, conduit 66, air-actuated control valve 68 and conduit 62 to provide a fluid flow path therebetween.

The carrier fluid source 32 is placed in fluid flow communication with the second inlet port of the sample valve 42 via conduit 70 and an air-actuated pump 72 and a pressure control valve 74 interposed therein, and via conduit 76 and a flow controller valve 78 interposed therein. Suitable pressure gauges 80 and 82 are connected respectively to conduits 70 and 76.

The process solvent source 34 is connected in fluid flow communication with the first outlet port of the sample valve 42 via conduit 84, air-actuated control valve 86 interposed therein and conduit 62. The portion of conduit 84 passing through the temperature controlled oven zone is preferably as short as possible and is preferably provided with a suitable thermal insulation covering as indicated at 84a.

The second output port of the valve body of the sample valve 42 is maintained in fluid flow communication with the inlet port 87 of a dilution chamber 88 via conduit 90. The outlet port 92 of the dilution chamber is maintained in fluid flow communication with the first inlet port of the valve body of the calibration or manual sample control valve 46 via conduit 94 and a suitable filter 96 interposed therein. The calibration or manual sample source 36 is connected in fluid flow communication with the second inlet port of the valve body of the sample control valve 46 via conduit 98. The second outlet port of the valve body of the sample control valve 46 is connected to a sample return conduit 100 which is routed to a suitable receiver (not shown). The third outlet port of the valve body of the sample control valve 46 is connected in fluid flow communication with the first inlet port of the valve body of sample valve 44 via conduit 102. The first outlet port of the valve body of the manual sample control valve 46 is connected in fluid communication with the first outlet port of the valve body of the second sample valve 44 via conduit 104.

The carrier fluid source 32 is connected in fluid flow communication with the second inlet port of the valve body of the second sample valve 44 via conduit 70, pump 72, pressure control valve 77, conduit 106 and flow controller valve 108 interposed in conduit 106. A pressure gauge 110 is connected in fluid communication with the conduit 106 intermediate the pressure controller valve 108 and the valve body of the second sample valve 44.

The second outlet port of the valve body of the second sample valve 44 is connected in fluid flow communication with the inlet port 112 of a first liquid chromatographic column 114 via conduit 116. The outlet port 118 of column 114 is connected in fluid flow communication with the inlet port 120 of a primary chromatographic column system 122 via conduit 124. The outlet port 126 of the chromatographic column system 122 is connected via conduit 128 to the sample inlet port 130 of a suitable detector 132. The sample outlet port 134 of the detector 132 is connected via conduit 136, conduit 138 and back pressure regulator valve 140 interposed in conduit 138 to a suitable carrier dump. A pressure gauge 142 is connected in fluid communication with the conduit 136. The first oulet port of the valve body of the second sample valve 44 is connected in fluid communication with the conduit 138 intermediate the back pressure regulator valve 140 and the carrier dump via conduit 104, conduit 144 and back pressure regulator valve 146 interposed in conduit 144. A pressure gauge 148 is connected in fluid communication with the conduit 144 intermediate the conduit 104 and the back pressure regulator valve 146.

The conduit 106 is connected in fluid flow communication with the carrier fluid reference inlet port 150 of the detector 132 via conduit 152, pressure controller valve 154 interposed in the conduit 152 and a flow restrictor 156 interposed in the conduit 152 intermediate the valve 154 and the detector 132. A pressure gauge 157 is connected in fluid communication with the conduit 152 intermediate the valve 154 and the flow restrictor 156. The reference outlet port 158 of the detector 132 is connected via conduit 159 to conduit 138. The pressure controller valve 154 and flow restrictor 156 act in consonance to provide flow regulation of carrier fluid passing therethrough to provide a substantially constant rate of carrier fluid flow to the detector 132.

As shown in FIG. 2, the previously described working fluid conduits are illustrated in heavy solid lines. Electrical conduits are illustrated by light solid lines and control air lines are illustrated by dashed lines. Zone boundaries defining the electronics zone 24, the temperature controlled oven zone 26 and the sample preparation zone 28 are illustrated by phantom lines.

The air-actuated control valves 54, 58, 64, 68 and 86 are normally open valves which are actuated to and maintained in their closed positions by the application of control air pressure thereto and are opened by releasing control air pressure therefrom. Valve 54 is connected via air conduit 160 to the common port of solenoid air valve 162. Valve 58 is connected via air conduit 164 to the common port of solenoid air valve 166. Valve 64 is connected via air conduit 168 to the common port of solenoid air valve 170. Valve 68 is connected via air conduit 172 to the common port of solenoid air valve 174. Valve 86 is connected via air conduit 176 to the common port of solenoid air valve 176. The normally open port of each of the solenoid air valves 162, 166, 170, 174 and 178 is connected via a suitable air conduit connected to the air source 30, while the normally closed ports of these solenoid air valves are vented to the atmosphere.

The position 1 actuator port 180 of the valve body of the first sample valve 42 is connected via air conduits 182 and 172 to the common port of solenoid air valve 174 while the position 2 actuator port 184 of the valve body of the first sample valve 42 is connected via air conduit 186 to the common port of solenoid air valve 188 while the normally closed port of the solenoid air valve 188 is connected by suitable air conduits to the air source 30.

The position 1 actuator port 190 of the valve body of the sample control valve 46 is connected via air conduit 192 to the common port of solenoid air valve 194 while the normally open port of the valve 194 is connected by suitable air conduits to the air source 30. The position 2 actuator port 196 of the valve body of the sample control valve 46 is connected via air conduit 198 to the common port of solenoid air valve 200 while the normally closed port of the solenoid air valve 200 is connected via suitable conduits to the air source 30.

The position 1 actuator port 202 of the valve body of the second sample valve 44 is connected via air conduit 204 to the common port of solenoid air valve 206 while the normally open port of the solenoid air valve 206 is connected via suitable air conduits to the air source 30. The position 2 actuator port 208 of the valve body of the sample valve 44 is connected via air conduit 210 to the common port of solenoid air valve 212 while the normally closed port of the solenoid air valve 212 is connected via suitable air conduits to the air source 30.

The normally open ports of solenoid air valves 188, 200 and 212, and the normally closed ports of solenoid air valves 194 and 206 are vented to the atmosphere.

The actuation of solenoid air valve 170 is controlled by relay 214 while the actuation of solenoid air valve 178 is controlled by relay 216. The simultaneous actuation of solenoid air valves 174 and 188 is controlled by relay 218. The simultaneous actuation of solenoid air valves 194 and 200 is controlled by relay 220. The simultaneous actuation of solenoid air valves 206 and 212 is controlled by relay 222. The selection of which of solenoid air valves 162 and 166 will be controlled by relay 224 is controlled by relay 226. Relays 214 through 224 are in the normally open positions shown in FIG. 2 when deenergized and are closed upon energization to provide a respective nominal 110 volt A.C. current through the corresponding coil of the associated solenoid air valve controlled thereby. Relay 226 completes a circuit from relay 224 through the actuating coil of solenoid air valve 162 when in the deenergized condition as shown in FIG. 2 and, alternately, completes an electrical circuit from relay 224 through the actuation coil of solenoid air valve 166 when in the energized position. Each of the relays 214 through 226 is responsive to a low voltage logic of about 5.4 volts d.c. from the programmer 12 for energization.

The carrier fluid pump 72 is driven by pressurized air provided from the air source 30 via air conduit 228 and air pressure regulator 230 interposed in the air conduit 228. An air pressure gauge 222 is connected to the air conduit 228 intermediate the pressure regulator 230 and a pump 72. It should be noted that the carrier fluid pump can be driven by any suitable means or pressurized carrier fluid can be provided by other suitable means.

In a preferred embodiment, the dilution chamber is provided with a capacity of approximately 800 microliters. The dilution chamber is preferably provided with suitable means for stirring or mixing the fluids passing therethrough. Within the dilution chamber is preferably a magnetic stirring bar which is secured at one end thereof such that the free end thereof is free to vibrate in a single plane. Vibration of the stirring bar within the dilution chamber is induced by an electric motor-driven magnetic vibrator (not shown) positioned outside the dilution chamber and which runs constantly during operation of the system 10.

The filter 96 can be of any suitable type for the filtration of the sample liquid and carrier liquid passing therethrough. In a preferred embodiment the filter is an in-line 0.2 micron filter.

The first liquid chromatographic column or precolumn 114 is preferably a relatively short gel permeation or size exclusion chromatographic column which can be readily removed from the conduit 116 for disposal should it become plugged. The precolumn 114 provides upstream protection for the primary chromatographic column system 122 from solid particles which might pass through the filter 96. Preferably the precolumn 114 is a size exclusion chromatographic column of approximately 2 to 3 inches in length which is charged with silica particles and preferably has a pore size of 500 Å.

The primary chromatographic column system comprises one or more gel permeation or size exclusion chromatographic columns. If two or more chromatographic columns are employed they are connected in series. In a preferred embodiment three size exclusion chromatographic columns are employed in the primary chromatographic column system 122, two of which have pore sizes of 500 Å and one of which has a pore size of 1000 Å.

Size exclusion chromatography is a form of liquid chromatography where separation occurs according to molecular size. Molecular permeation through a solvent-filled, packed column containing silica particles with a distribution of pore sizes results in exclusion of large molecules which cannot penetrate the pores. Consequently, the large molecules elute from the column prior to the elution of the smaller particles which permeate the silica matrix and travel greater path lengths before elution. Separation is, therefore, accomplished strictly by molecular size and over a specified range of sizes. Gel permeation chromatographic columns and size exclusion chromatographic columns generally operate in the same manner. Gel permeation columns are columns which are packed with crosslinked polystyrene particles while size exclusion chromatographic columns are columns which are packed with silica particles.

In a preferred embodiment, the sample loop 48 has a volume of approximately 30 microliters, the sample loop 50 has a volume of approximately 225 microliters and the dilution chamber has a volume of approximately 800 microliters. Carrier liquid flow to the dilution chamber is regulated by the flow of controller valve 78 to a flow rate of about 0.5 milliliters per minute within about ±0.25 percent. Carrier liquid flow to the chromatographic columns 114 and 122 is regulated by the flow controller valve 108 to a flow rate of about 1 milliliter per minute within a range of about ±0.25 percent. Carrier liquid flow through the pressure control valve 154 and flow restrictor 156 to the detector 132 is preferably maintained at a flow rate of approximately 0.25 milliliters per minute.

The temperature in the temperature controlled oven zone 26 can be any suitable temperature selected for the sample liquid being analyzed and the diluent or carrier fluid employed. It is desirable that the temperature be maintained slightly above the maximum ambient temperature to which the analyzer will be subjected but below the minimum boiling temperature of the sample liquid, carrier liquid or process solvent which will be subjected to such temperature. In a preferred embodiment, a suitable temperature is approximately 60° C. (140° F.).

The operation sequence of the liquid chromatographic analyzer system 10 is controlled by the programmer unit 12. Initially, the relays and valves are in the condition illustrated in FIG. 2. The operation sequence is initiated when the programmer unit 12 receives a signal indicating that either reactor 38 or reactor 40 is ready for sampling. Assuming reactor 38 to be ready for sampling, the programmer unit 12, in response to such signal, stores the reactor number and selects the appropriate program and, in response to the program, initiates the analysis cycle by energizing relay 224 thus venting solenoid air valve 162 to the atmosphere and opening control valve 54 which simultaneously energizing relays 214 and 218 causing control valves 64 and 68 to open and causing the valve member of the first sample valve 42 to move to the second position illustrated by the dashed lines. Under these conditions product from reactor 38 is permitted to flush out the sample line with the exception of the loop 48 through the sample valve 42. After a predetermined time for such flushing, relay 218 is deenergized, thus causing the simultaneous closing of control valve 68 and the movement of the valve member of the sample valve 42 back to the first position causing the product sample stream to be forced through the sample loop 48 of the control valve 42. After a predetermined delay, relay 214 is deenergized causing control valve 64 to close, thus applying back pressure to the product stream to raise the pressure of the fluid within the sample loop 48 for the prevention of the formation of bubbles in the sample loop 48. Subsequently, relay 218 is again energized at a time $t_1$ thereby opening control valve 68 and moving the valve member of the sample valve 42 to the second position where the contents of the sample loop 48 are injected into the dilution stream of carrier liquid or diluent which has been constantly flowing through the system. Relay 216 is then energized to open control valve 86 to permit process solvent to flush the sample lines 62, 66 and 52 back to the reactor 38. After a suitable time increment for such flushing, relay 224 is deenergized to close the control valve 54 to the reactor 38 and relay 214 is simultaneously energized to open control valve 64 to permit the process solvent to flush sample liquid from conduit 62 and sample return line 60.

After the sample from the sample loop 48 of the sample valve 42 enters the dilution chamber 88 with the diluent or carrier liquid stream it is diluted therein to achieve a desired ratio of carrier liquid to sample liquid. The concentration of sample liquid in the stream of carrier liquid and sample liquid initially increases at a very high rate but decreases exponentially with time as the stream passes through the dilution chamber with the concentration approaching a substantially constant ratio of carrier or diluent liquid to sample liquid. The diluted sample passes through the filter 96 and valve 46 and into the sample loop 50 of the second sample valve 44. At a predetermined time $t_2$, relay 222 is energized to position the valve member of sample valve 44 in the second position indicated by the dashed lines to inject the diluted sample into the carrier liquid stream flowing to the chromatographic columns 114 and 122. The time period $t_2-t_1$ is predetermined so as to sample the diluted sample liquid at a time when the concentration ratio is exponentially decaying. The precolumn 114 protects the main columns 122 from undissolved components which might cause plugging of the main columns. The sample liquid and carrier liquid are separated in the chromatographic columns according to molecular size, the larger molecules eluting first from the chromatographic column system 122 followed by successively smaller molecules. The column effluent from the primary chromatograhic column system 122 enters the detector 132 and is detected using a dielectric detector. The carrier liquid entering the reference inlet port 150 of the detector 132 is also detected using a dielectric detector and the detector 132 then distinguishes the sample components from the carrier liquid in a conventional manner. The results of this analysis are then provided to the programmer unit 12 by suitable means (not shown) which in turn causes the results to be presented on the tape of the digital printer 20 and to be graphically represented on the strip chart recorder 22.

Provisions are also made in the liquid chromatographic analyzer system 10 to run a calibration sample. This is done by attaching a pressurized container containing a calibration sample to the conduit 98 connected to the second inlet port of the calibration and manual sample control valve 46. The program in the programmer unit 12 is then activated by a "calibrate" pushbutton switch (not shown). The programmer then energizes relay 220 to position the valve member of the valve 46 in its second position illustrated by the dashed lines to charge the calibration sample through the sample loop 50 of the sample valve 44 which is in its first position with the relay 222 deenergized. Relay 222 is then energized to position the valve 44 in the second position introducing the calibration sample into the carrier stream to the chromatographic columns and detector. The results of the detector analysis are then recorded and displayed in the manner described above.

In a manner similar to that described for the analysis of a calibration sample, a manually prepared liquid product sample can also be injected through conduit 98 to the second inlet port of the valve 46. This operation is initiated by a "manual" pushbutton switch (not shown) on the programmer unit and involves essentially the same cycle as that described above for the calibration sample except that the printout provided by the printer 20 is suitable for a product sample rather than a calibration sample. The analog strip chart recorder 22 also displays the results of each analysis of a manually prepared liquid product sample.

In all the analysis cycles described above, the effluent from the detector 132 is conducted therefrom through conduits 136, 159 and 138 and back pressure regulator valve 140 to a suitable carrier dump.

For the chromatographic analysis of hydrocarbon liquid samples which have relatively low dielectric constants ranging from about 1.8 to about 2.2, it is desirable to select a diluent or carrier liquid having a relatively high dielectric constant preferably in the range from about 6.5 to about 7.5 so as to readily distinguish the constituents of the sample liquid from the carrier liquid in the detector 132. Suitable diluents or carrier liquids include tetrahydrofuran and ethyl acetate.

It will be understood that while a dielectric detector is employed in the system of the present invention, other detectors may be employed as may be required for proper analysis of various sample liquids.

In the presently preferred embodiment, automatic size exclusion chromatographic analysis of a process liquid sample requires a total time of approximately 30 minutes. This time period is roughly divided into about 8 minutes for sample preparation and about 22 minutes for analysis of the sample.

At the end of each of the cycles described above, the programmer unit 12 automatically resets the relays, solenoid air valves, and sample valves to the condition illustrated in FIG. 2 in anticipation of the next signal indicating a reactor ready for sampling or a manually prepared product sample or a calibration sample ready for analysis. It will be readily apparent that, while two reactors are shown as being monitored by the system 10, any number of reactors can be monitored by the system through the addition of additional control relays, air control valves and reactor control valves connecting lines. It is to be understood that the specific embodiment of the present invention shown in the drawing and described above has been provided for the purpose of illustration of the broad invention. Further variations and modifications of the structure, materials, and uses disclosed can be made without departing from the scope of the claimed invention.

That which is claimed is:

1. An apparatus for providing diluted samples from a fluid sample source and a fluid diluent source, said apparatus comprising:

first conduit means having first and second ends with the first end thereof in flow communication with said fluid sample source for providing a path for flow of sample fluid therethrough from said fluid sample source;

second conduit means having first and second ends with the first end thereof in flow communication with said fluid diluent source for providing a path for flow of a diluent fluid stream therethrough from said fluid diluent source;

a first sample valve body, having first, second and third inlet ports and first, second and third outlet ports, with the first inlet port thereof in flow communication with the second end of said first conduit means and with the second inlet port thereof in flow communication with the second end of said second conduit means;

third conduit means having first and second ends with the first end thereof in flow communication with the first outlet port of said first sample valve body for providing a path for flow of fluid therethrough;

fourth conduit means having first and second ends with the first end thereof in flow communication with the second outlet port of said first sample valve body for providing a path for flow of fluid therethrough;

fifth conduit means having first and second ends with the first end thereof in flow communication with the third outlet port of said first sample valve body and with the second end thereof in flow communication with the third inlet port of said first sample valve body for providing a path for flow of fluid therethrough;

first sample valve member means operatively related to said first sample valve body for placing in flow communication said first inlet port with said third outlet port, said second inlet port with said second outlet port and said third inlet port with said first outlet port, and, alternately, for placing in flow communication said first inlet port with said first outlet port, said second inlet port with said third outlet port, and said third inlet port with said second outlet port, so as to inject a predetermined quantity of said sample fluid into said diluent fluid stream emanating from the second outlet port of said first sample valve body;

dilution chamber means having an inlet port and an outlet port with the inlet port thereof in flow communication with the second end of said fourth conduit means for mixing said predetermined quantity of said sample fluid with said diluent fluid stream;

sixth conduit means having first and second ends with the first end thereof in flow communication with the outlet port of said dilution chamber means for providing a path for flow of fluid from said dilution chamber means;

a second sample valve body, having first, second and third inlet ports and first, second and third outlet ports, with the first inlet port thereof in flow communication with the second end of said sixth conduit means;

seventh conduit means having first and second ends with the first end thereof in flow communication with a carrier fluid source and with the second end thereof in flow communication with the second inlet port of said second sample valve body for providing a flow path for flow of carrier fluid from said carrier fluid source;

eighth conduit means having first and second ends with the first end thereof in flow communication with the first outlet port of said second sample valve body for providing a flow path for fluid from said second sample valve body;

ninth conduit means having first and second ends with the first end thereof in flow communication with the second outlet port of said second sample valve body for providing a flow path for fluid from said second sample valve body;

tenth conduit means having first and second ends with the first end thereof in flow communication with the third outlet port of said second sample valve body and with the second end thereof in flow communication with the third inlet port of said second sample valve body for providing a path for flow of fluid therethrough; and second sample valve member means operatively related to said second sample valve body for placing in fluid communication said first inlet port of said second sample valve body with said third outlet port of said second sample valve body, said second inlet port of said second sample valve body with said second outlet port of said second sample valve body, and said third inlet port of said second sample valve body with said first outlet port of said second sample valve body, and, alternately, for placing in fluid communication said first inlet port of said second sample valve body with said first outlet port of said second sample valve body, said second inlet port of said second sample valve body with said third outlet port of said second sample valve body, and said third inlet port of said second sample valve body with said second outlet port of said second sample valve body, so as to inject a predetermined quantity of said mixed sample fluid and diluent fluid stream emanating from said dilution chamber means into the carrier fluid emanating from said carrier fluid source.

2. An apparatus is accordance with claim 1 wherein said ninth conduit means is characterized further to include at least one column means interposed intermediate the first and second ends thereof for making at least one molecular size separation of the molecules of the fluid flowing therethrough.

3. An apparatus according to claim 2 wherein said sixth conduit means is characterized further to include filter means interposed therein intermediate the first and second ends thereof for filtering fluid flowing therethrough.

4. An apparatus in accordance with claim 1 wherein:
said second conduit means is characterized further to include first flow control means interposed therein intermediate the first and second ends thereof for controlling the diluent fluid stream flowing therethrough so as to maintain a substantially constant rate of flow of diluent fluid therethrough; and
said seventh conduit means is characterized further to include second flow control means interposed therein intermediate the first and second ends thereof for controlling the flow of carrier fluid therethrough so as to maintain a substantially constant rate of flow of carrier fluid therethrough.

5. An apparatus in accordance with claim 4 characterized further to include:
valve member control means operatively related to said first sample valve member means and said second sample valve member means for automatically actuating said second sample valve member means a predetermined time after automatically actuating said first sample valve member means so as to inject said predetermined quantity of said mixed sample fluid and diluent fluid stream into said carrier fluid stream a predetermined time after the injection of said predetermined quantity of said sample fluid into said diluent fluid stream 6. A liquid chromatographic analysis apparatus comprising:
an apparatus in accordance with claim 4;
column means in flow communication with the second end of said ninth conduit means for effecting the separation of components of a fluid sample;

detector means in flow communication with said column means for detecting the components of a fluid sample from said column means; and means for actuating said first and second sample valve member means to effect the trapping of diluted samples and the movement of the thus trapped diluted samples through said column means.

7. An apparatus in accordance with claim 6 characterized further to include:

carrier fluid conduit means having first and second ends with the first end thereof in flow communication with said detector means and with the second end thereof in flow communication with a carrier fluid source for providing a flow path for flow of carrier fluid from said carrier fluid source to said detector means.

8. An apparatus in accordance with claim 7 characterized further to include:

flow regulation means interposed in said carrier fluid conduit means for regulating the flow of carrier fluid through said carrier fluid conduit means so as to maintain a substantially constant rate of flow of carrier fluid to said detector means.

9. An apparatus in accordance with claim 8 wherein said flow regulation means is characterized further to include:

pressure control means for maintaining a substantially constant carrier fluid pressure in said carrier fluid conduit means between said pressure control means and said detector means; and flow restriction means intermediate said pressure control means and said detector means for restricting flow of carrier fluid to said detector means through said carrier fluid conduit means.

10. An apparatus in accordance with claim 1 wherein said sixth conduit means is characterized further to include:

valve means interposed therein intermediate the first and second ends thereof and movable between a first position and a second position for placing the first and second ends of said sixth conduit means in fluid communication when said valve means is in the first position and, alternately, for blocking fluid communication between the first and second ends of said sixth conduit means and placing the second end of said sixth conduit means in fluid communication with a second sample source when said valve means is in the second position.

11. An apparatus in accordance with claim 1 characterized further to include:

eleventh conduit means having first and second ends with the first end thereof in flow communication with said first inlet port of said first sample valve body and with the second end thereof in flow communication with said first outlet port of said first sample valve body for providing a path for fluid flow therethrough, said eleventh conduit means including first valve means interposed therein intermediate the first and second ends thereof for opening said eleventh conduit means to fluid flow therethrough in a first position of said first valve means and, alternately, for closing said eleventh conduit means to fluid flow therethrough in a second position of said first valve means;

twelfth conduit means having first and second ends with the first end thereof in flow communication with a source of solvent and with the second end thereof in flow communication with the first outlet port of said first sample valve body for providing a path for flow of fluid therethrough, said twelfth conduit means including second valve means interposed therein intermediate the first and second ends thereof for opening said eleventh conduit means to fluid flow therethrough in a first position of said second valve means and, alternately, for closing said twelfth conduit means to fluid flow therethrough in a second position of said second valve means;

said third conduit means including third valve means interposed therein intermediate the first and second ends thereof for opening said third conduit means to fluid flow therethrough in a first position of said third valve means and, alternately, for closing said third conduit means to fluid flow therethrough in a second position of said third valve means; and said first conduit means including fourth valve means interposed therein intermediate the first and second ends thereof for opening said first conduit means to fluid flow therethrough in a first position of said fourth valve means and, alternately, for closing said first conduit means to fluid flow therethrough in a second position of said fourth valve means.

12. An apparatus in accordance with claim 4 characterized further to include:

control means operatively connected to said first sample valve member means, said first valve means, said second valve means, said third valve means and said fourth valve means for automatically and sequentially:

placing said first sample valve member means in the second position thereof, placing each of said first, third and fourth valve means in the first position thereof, and placing said second valve means in the second position thereof;

actuating said sample valve member means to the first position thereof and actuating said first valve means to the second position thereof;

actuating said third valve means to the second position thereof;

actuating said first sample valve member means to the second position thereof and actuating said first valve means to the first position thereof;

actuating said second valve means to the first position thereof; and actuating said third valve means to the first position thereof and actuating said fourth valve means to the second position thereof.

13. An apparatus in accordance with claim 11 characterized further to include:

control means operatively connected to said first sample valve member means, said first valve means, said second valve means, said third valve means and said fourth valve means for automatically and sequentially:

placing said first sample valve member means in the first position thereof and placing each of said first, second, third and fourth valve means in the second position thereof;

actuating said first sample valve member means to the second position thereof and actuating each of said first, third and fourth valve means to the first position thereof;

actuating said first sample valve member means to the first position thereof and actuating said first valve means to the second position thereof;

actuating said third valve means to the second position thereof;

actuating said first sample valve member means to the second position thereof and actuating said first valve means to the first position thereof;

actuating said second valve means to the first position thereof;

actuating said third valve means to the first position thereof and actuating said fourth valve means to the second position thereof; and actuating said first sample valve member means to the first position thereof and actuating each of said first, second and third valve means to the second position thereof.

14. A method of intermittently effecting chromatograhic analysis of a sample liquid employing an apparatus according to claim 11, comprising:

passing a stream of liquid diluent into said dilution chamber means at a substantially constant flow rate;

passing a stream of a sample liquid from said fluid sample source through said fifth conduit means;

raising the pressure of said sample liquid in said fifth conduit means;

traping a specific volume of said sample liquid in said fifth conduit means and injecting said specific volume of said sample liquid into said stream of liquid diluent at a time $t_1$;

directing a stream of solvent from said source of solvent via said twelfth conduit means, said eleventh conduit means and said first conduit means to said fluid sample source so as to purge sample liquid from said eleventh conduit means and said first conduit means;

directing a stream of solvent through said twelfth conduit means and said third conduit means so as to purge said sample liquid from said third conduit means;

mixing said specific volume of said sample liquid with said stream of liquid diluent in said dilution chamber means so as to produce a diluted effluent stream having a concentration of sample liquid which exponentially decays with time after a concentration peak to a substantially constant concentration value;

trapping a specific volume of said diluted effluent stream at an exponentially decaying concentration value in said tenth conduit means at a predetermined time $t_2$ and injecting said thus trapped specific volume of said diluted effluent into a stream of carrier fluid at said predetermined time $t_2$, the time period $t_2-t_1$ being predetermined so as to obtain said trapped specific volume of said diluted effluent when the concentration of sample liquid therein is a substantially constant value, and so as to produce a further diluted effluent stream;

effecting chromatographic separation of at least some of the components of said further diluted effluent stream so as to elute a thus separated effluent stream; and detecting at least one characteristic of the components of the thus separated effluent stream.

15. A liquid chromatographic analysis apparatus comprising:

an apparatus in accordance with claim 1;

column means in flow communication with the second end of said ninth conduit means for effecting the separation of components of a liquid sample;

detector means in flow communication with said column means for detecting the components of a fluid sample from said column means; and means for actuating said first and second sample valve member means to effect the trapping of diluted samples and the movement of such diluted samples through said column means.

16. A method of intermittently effecting chromatographic analysis of a sample liquid comprising:

passing a stream of liquid diluent through a dilution chamber at a substantially constant flow rate;

injecting a specific volume of a sample liquid into said stream of liquid diluent upstream of said dilution chamber at a time $t_1$;

mixing said specific volume of sample liquid with said liquid diluent in said dilution chamber so as to produce a diluted effluent stream having a concentration of sample liquid which exponentially decays with time after a concentration peak to a substantially constant concentration value;

trapping a specific volume of said diluted effluent stream at an exponentially decaying concentration value at a time $t_2$; and effecting chromatographic separation of said trapped volume of diluted effluent stream.

17. A method in accordance with claim 16 wherein said flow rate of said diluent stream is about 0.5 milliliters per minute and the time $t_2-t_1$ is about 4 minutes.

* * * * *

UNITED STATES PATENT AND TRADEMARK OFFICE
CERTIFICATE OF CORRECTION

PATENT NO. : 4,186,607

DATED : February 5, 1980

INVENTOR(S) : Grady T. Porter et al

It is certified that error appears in the above-identified patent and that said Letters Patent are hereby corrected as shown below:

Column 14, claim 12, line 26, after "claim" change "4" to --- 11 ---.

Signed and Sealed this

Tenth Day of March 1981

[SEAL]

Attest:

RENE D. TEGTMEYER

*Attesting Officer*    *Acting Commissioner of Patents and Trademark*